United States Patent [19]

Takaya et al.

[11] 4,354,022
[45] Oct. 12, 1982

[54] PROCESS FOR PREPARING 3-METHYLENECEPHAM COMPOUNDS OR A SALT THEREOF

[75] Inventors: Takao Takaya, Kawanishi; Takashi Masugi, Ikeda; Toshiyuki Chiba, Osaka; Akiteru Yoshioka, Kyoto; Masayuki Kato, Mino; Ikuo Ueda, Toyonaka; Masakazu Kobayashi, Ikeda, all of JPX

[73] Assignee: Fujisawa Pharmaceutical Co., Ltd., Osaka, Japan

[21] Appl. No.: 270,876

[22] Filed: Jun. 5, 1981

[51] Int. Cl.³ .................................. C07D 501/04
[52] U.S. Cl. .................................. 544/28; 544/30; 544/22; 544/16; 424/246
[58] Field of Search .................. 544/28, 27, 16, 26, 544/22, 28; 424/246

[56] References Cited
U.S. PATENT DOCUMENTS 3,792,995  2/1974  Ochiai et al. ............... 260/243 C
3,932,393  1/1976  Chauvette .................. 260/243 C

FOREIGN PATENT DOCUMENTS 50-105682  8/1975  Japan .

Primary Examiner—Nicholas S. Rizzo
Attorney, Agent, or Firm—Oblon, Fisher, Spivak, McClelland & Maier

[57] ABSTRACT

A new process for preparing 3-methylenecepham compounds of the formula:

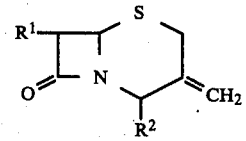

wherein
  $R^1$ is amino or a protected amino group, and
  $R^2$ is a carboxy or a protected carboxy group,
or a salt thereof,
which comprises reducing a compound of the formula:

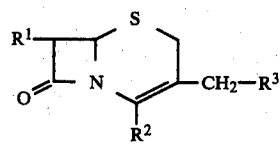

wherein
  $R^1$ and $R^2$ are each as defined above, and
  $R^3$ is halogen or heterocyclicthio which may have suitable sutstituent, or a salt thereof, with a combination of a metal selected from the group consisting of zinc, tin and iron, and an ammonium salt of an acid selected from the group consisting of ammonium halide, ammonium carbonate and ammonium acetate, said 3-methylenecepham compounds being useful as intermediates for preparing antimicrobially active 3-cephem compounds.

8 Claims, No Drawings

PROCESS FOR PREPARING 3-METHYLENECEPHAM COMPOUNDS OR A SALT THEREOF

The present invention relates to a new process for preparing 3-methylenecepham compounds or a salt thereof. More particularly, the present invention relates to a new process for preparing 3-methylenecepham compounds which are useful as intermediate compounds for preparing antimicrobially active 3-cephem compounds, e.g. 7-[2-(2-aminothiazol-4-yl)-2-methoxyiminoacetamido]-3-cephem-4-carboxylic acid (syn isomer) or its pharmaceutically acceptable salt as disclosed in the specification of European Patent Publication Number 9671.

According to the present invention, 3-methylenecepham compounds of the formula:

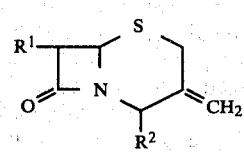

wherein
$R^1$ is amino or a protected amino group, and
$R^2$ is carboxy or a protected carboxy group,
or a salt thereof, can be prepared by reducing a compound of the formula:

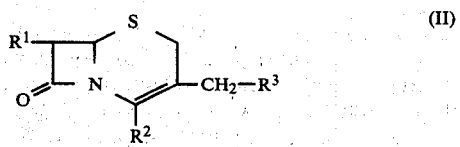

wherein
$R^1$ and $R^2$ are each as defined above, and
$R^3$ is halogen or heterocyclicthio which may have suitable substituent(s),
or a salt thereof,
with a combination of a metal and ammonium salt of an acid.

It is known to produce the compound (I) from the compound (II) by electrolytic reduction (Japanese Patent Publication No. 5396/1976; hereinafter referred to as "Prior art A"), or by catalytic reduction or chemical reduction using a combination of a metal and an acid (Japanese Unexamined Patent Publication No. 20188/1972; hereinafter referred to as "Prior art B"), or by chemical reduction using a combination of a metal and an acid (Japanese Unexamined Patent Publication No. 105682/1975; hereinafter referred to as "Prior art C").

According to known processes, however, yields are low [Sodium 7-(1H-tetrazol-1-ylacetamido)-3-methylenecepham-4-carboxylate is obtained from sodium 7-(1H-tetrazol-1-ylacetamido)-3-(5-methyl-1,3,4-thiadiazol-2-yl)thiomethyl-3-cephem-4-carboxylate in about 10% yield in Example 10 of the Prior Art A, and 7-(2-thienylacetamido)-3-methylenecepham-4-carboxylic acid is obtained from sodium 7-(2-thienylacetamido)-3-(1-methyl-1H-tetrazol-5-yl)thiomethyl-3-cephem-4-carboxylate in about 35% or 49% yield in Examples 11 and 12 of the Prior Art B], and much amount of 3-methyl-3-cephem compounds are produced as by-products which make the purity of the object compound (I) low.

Accordingly, it is very desirable to provide a method for producing the object compound (I) in high yields and good purity, which is achieved by the present invention.

Suitable salts of the object compound (I) and the starting compound (II) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, cinnamate, P-chlorocinnamate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent description of the present specification, suitable examples and illustrations of the various difinitions of the present invention are explained in details as follows.

The term "lower" in the present specification is intended to mean a group having 1 to 6 carbon atom(s) and the term "higher" is intended to mean a group having 7 to 18 carbon atoms, unless otherwise provided.

Suitable "a protected amino group" may include an amino group substituted with a suitable protective group which is conventionally used in cephalosporin and penicillin compounds as a protective group of the amino group at their 7th or 6th position, and suitable "a protected amino group" may include acylamino, phenyl(lower)alkylamino (e.g. benzylamino, tritylamino, etc.), and the like.

Suitable "acyl moiety" in the term "acylamino" may include aliphatic acyl group and acyl group containing an aromatic ring, which is referred to as aromatic acyl, or heterocyclic ring, which is referred to as heterocyclic acyl.

Suitable example of said acyl may be illustrated as follows:
Aliphatic acyl such as lower or higher alkanoyl (e.g. formyl, acetyl, propionyl, butyryl, valeryl, hexanoyl, heptanoyl, stearoyl, etc.);
lower or higher alkoxycarbonyl (e.g. methoxycarbonyl, ethoxycarbonyl, t-butoxycarbonyl, t-pentyloxycarbonyl, heptyloxycarbonyl, etc.);
lower or higher alkanesulfonyl (e.g. methanesulfonyl, ethanesulfonyl, etc.); or the like;
Aromatic acyl such as
aroyl (e.g. benzoyl, toluoyl, naphthoyl, etc.);
ar(lower)alkanoyl such as phenyl(lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl such as phenoxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as
heterocycliccarbonyl (e.g. thenoyl, furoyl, nicotinoyl, etc.);

heterocyclic(lower)alkanoyl (e.g. thienylacetyl, thiazolylacetyl, tetrazolylacetyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered(more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered(more preferably 5 or 6-membered)heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered(more preferably 5 or 6-membered)-heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered(more preferably 5 or 6-membered)heteromonocyclic group containing 1 to 2 sulfur atom(s) and 1 to 3 nitrogen atom(s), for example, thiazolidinyl, etc.;

unsaturated 3 to 8-membered(more preferably 5 or 6-membered)heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered(more preferably 5 or 6-membered)heteromonocyclic group containing an oxygen atom, for example, furyl, etc.;

unsaturated 3 to 8-membered(more preferably 5 or 6-membered)heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety thus defined may optionally be substituted by one to ten, same or different, suitable substituent(s) such as:

lower alkyl (e.g. methyl, ethyl, etc.);
lower alkoxy (e.g. methoxy, ethoxy, propoxy, etc.);
lower alkylthio (e.g. methylthio, ethylthio, etc.);
lower alkylamino (e.g. methylamino, etc.);
cyclo(lower)alkyl (e.g. cyclopentyl, cyclohexyl, etc.);
cyclo(lower)alkenyl (e.g. cyclohexenyl; cyclohexadienyl, etc.); hydroxy; halogen (e.g. chloro, bromo, etc.); amino; protected amino as aforementioned; cyano; nitro; carboxy; protected carboxy as mentioned below; sulfo; sulfamoyl; imino; oxo; amino(lower)alkyl (e.g. aminomethyl, aminoethyl, etc.); or the like.

Suitable "protected carboxy group" may include a carboxy group substituted with a conventional protective group which is conventionally used in cephalosporin and penicillin compounds as the carboxy-protective group of the carboxy group at their 4th or 3rd position, for example, esterified carboxy group.

Suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.);

lower cycloalkyl(lower)alkyl ester (e.g. 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxy(lower)alkyl ester (e.g., methoxymethyl ester, ethoxymethyl ester, isopropoxymethyl ester, 1-methoxyethyl ester, 1-ethoxyethyl ester, etc.);

lower alkylthio(lower)alkyl ester (e.g., methylthiomethyl ester, ethylthiomethyl ester, ethylthioethyl ester, isopropylthiomethyl ester, etc.);

mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethylester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester etc.);

ar(lower)alkyl ester, for example, mono(or di or tri)-phenyl(lower)alkyl ester optionally substituted by one or more suitable substituent(s) such as nitro, hydroxy, lower alkoxy or the like (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester optionally substituted by one or more suitable substituent(s) such as alkyl-substituted or unsubstituted phenyl ester optionally substituted by halogen, lower alkoxy or the like (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; and the like.

Suitable "halogen" may include chlorine, bromine, iodine and the like.

Suitable "heterocyclic" moiety in the term "heterocyclicthio" group means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered(more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), triazinyl (e.g. 2,5-dihydro-1,2,4-triazinyl, 1,2,4-triazinyl, etc.), etc.;

saturated 3 to 8-membered(more preferably 5 or 6-membered)heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered(more preferably 5 or 6-membered)heteromonocyclic group containing 1 to 2-oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered(more preferably 5 or 6-membered)heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered(more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered(more preferably 5 or 6-membered)heteromonocyclic group containing 1 to 2 sulfur atom(s) and 1 to 3 nitrogen atom(s), for example, thiazolidinyl, etc.;

unsaturated 3 to 8-membered(more preferably 5 or 6-membered)heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered(more preferably 5 or 6-membered)heteromonocyclic group containing an oxygen atom, for example, furyl, etc.;

unsaturated 3 to 8-membered(more preferably 5 or 6-membered)heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

Thus defined heterocyclic group may optionally have one or more suitable substituent(s) such as lower alkyl (e.g., methyl, ethyl, propyl, isopropyl, butyl, isobutyl, pentyl, cyclopentyl, hexyl, cyclohexyl, etc.); lower alkylthio (e.g., methylthio, ethylthio, propylthio, etc.); lower alkenyl (e.g., vinyl, allyl, butenyl, etc.); carboxy; carboxy(lower)alkyl (e.g. carboxymethyl, carboxyethyl, carboxypropyl, etc.); hydroxy(lower)alkyl (e.g. hydroxymethyl, hydroxyethyl, hydroxypropyl, etc.); amino(lower)alkyl (e.g. aminomethyl, aminoethyl, aminopropyl, aminobutyl, etc.); protected amino(lower)alkyl (e.g. acylaminomethyl, acylaminoethyl, acylaminopropyl, acylaminobutyl therein acyl moieties are as defined above, etc.) or the like.

The process for the preparation of the object compound (I) of the present invention is explained in detail in the following.

Process

The object compound (I) or a salt thereof can be prepared by reducing the compound (II) or a salt thereof, with a combination of a metal and ammonium salt of an acid.

Suitable metal may include zinc, tin, iron and the like.

Suitable ammonium salt of an acid may include ammonium halide (e.g. ammonium chloride, ammonium bromide, etc.), ammonium carbonate, ammonium acetate, and the like.

The present reaction is usually carried out in a conventional solvent which does not adversely influence the reaction such as N,N-dimethylformamide, water, chloroform, acetonitrile, dioxane, N,N-dimethylacetamide or the like. These solvents may be used as a mixture thereof. Among the above solvents, preferred one is N,N-dimethylformamide. The present reaction is often preferably carried out in the presence of thiourea.

When the starting compound (II) is used in a form of the free acid in the present reaction, it is preferable that the free carboxy group(s) of the starting compound (II) is protected before the present reduction, for example, the starting compound (II) is treated with an esterification reagent such as silyl compound [e.g., bis(trimethylsilyl)acetamido, trimethylsilylacetamido, etc.] or the like before the present reduction.

The reaction temperature is not critical and the reaction is preferably carried out under cooling to at ambient temperature.

The following examples and references are given for the purpose of illustrating the present invention.

EXAMPLE 1

7-Amino-3-(1-methyl-1H-tetrazol-5-yl)thiomethyl-3-cephem-4-carboxylic acid (6.56 g; purity 88.9%) and trimethylsilylacetamide (10.8 g) were dissolved in N,N-dimethylformamide (26 ml) at ambient temperature, and the solution was cooled with ice-water. After the addition of ammonium chloride (16.1 g) and zinc powder (10.8 g), the mixture was stirred for 40 minutes under ice-cooling.

The reaction mixture was filtered, and the residue was washed with N,N-dimethylformamide (15 ml). The filtrate and the washing were combined, and mixed with diisopropyl ether (50 ml), acetic acid (1 ml) and n-hexane (7 ml), and allowed to stand under ice-cooling to separate into two layers. The upper layer removed and water (30 ml) was added remaining layer, and then adjusted to pH 3.7 with conc. hydrochloric acid. The precipitates were collected by filtration, washed with cold water (3 ml) and dried under reduced pressure to give 7-amino-3-methylenecepham-4-carboxylic acid (purity: 79.8%) in a yield of 85.5%.

I.R. (Nujol): 3200–2000, 1770, 1620 (sh), 1540 (sh), 1460, 1220, 1140 cm$^{-1}$

N.M.R. (NaHCO$_3$+D$_2$O, δ): 3.37, 3.72 (d,d, 2H, J=14 Hz), 5.00 (1H, s), 5.28 (1H, s), 5.33 (1H, d, J=3 Hz), 5.35 (1H, s), 5.42 (1H, d, J=3 Hz)

Similar result was obtained by using 7-amino-3-(5-methyl-1,3,4-thiadiazol-2-yl)thiomethyl-3-cephem-4-carboxylic acid instead of 7-amino-3-(1-methyl-1H-tetrazol-5-yl)thiomethyl-3-cephem-4-carboxylic acid in the Example 1.

EXAMPLE 2

Benzhydryl 7-amino-3-chloromethyl-3-cephem-4-carboxylate (10.0 g) was dissolved in N,N-dimethylformamide (60 ml). The mixture was cooled to −10° C. To the mixture was added zinc powder (2.29 g), and a solution of ammonium chloride (3.22 g) in water (10 ml) was added dropwise thereto at −10° to −3° C. under stirring, which was continued for 30 minutes at the same temperature. The reaction mixture was poured into a mixture of water (200 ml) and ethyl acetate (200 ml), and an insolble material was filtered off. The organic layer was separated out, washed with a saturated aqueous solution of sodium chloride, dried over magnesium sulfate and concentrated under reduced pressure. To the residue was added a solution of p-toluenesulfonic acid (5.0 g) in ethyl acetate (200 ml). The mixture was stirred under ice-cooling, and the resulting precipitates were collected by filtration, washed with ethyl acetate and dried to give benzhydryl 7-amino-3-methylenecepham-4-calboxylate p-toluene-sulfonate (12.7 g).

EXAMPLE 3

To N,N-dimethylformamide (15 ml) were added thiourea (0.73 g) and a solution of ammonium chloride (0.51 g) in water (1 ml), and the mixture was stirred at 5° C.

To the mixture was added benzhydryl 7-amino-3-chloromethyl-3-cephem-4-carboxylate (2.0 g). The mixture was cooled to −10° C. and zinc powder (0.6 g) was added thereto. The mixture was stirred for 30 minutes at −10° to −8° C. and poured into a mixture of ethyl acetate (200 ml) and an aqueous solution of sodium chloride (100 ml), and an insolble material was filtered off. The organic layer was separated out, washed with a saturated aqueous solution of sodium chloride and concentrated. The residue was dissolved in ethyl acetate (80 ml). To the solution was added a solution of p-toluenesulfonic acid (1.0 g) in ethyl acetate (15 ml).

The mixture was stirred under ice-cooling. The resulting precipitates were collected by filtration, washed with ethyl acetate and dried to give benzhydryl 7-amino-3-methylenecepham-4-calboxylate p-toluenesulfonate (2.2 g), mp. 161° to 163° C.

I.R. (Nujol): 1780, 1740 cm$^{-1}$

N.M.R. (DMSO-d$_6$, δ): 2.28 (3H, s), 3.50 (2H, ABq, J=14 Hz), 5.02 (1H, d, J=5 Hz), 5.32 (1H, d, J=5 Hz), 5.40 (2H, s), 5.58 (1H, s), 6.88 (1H, s), 7.38 (10H, m), 8.8 (2H, m)

EXAMPLE 4

To a solution of benzhydryl 7-amino-3-(5-methyl-1,3,4-thiadiazol-2-yl)thiomethyl-3-cephem-4-carboxylate (1.0 g) in N,N-dimethylformamide (10 ml) were added ammonium chloride (1.0 g) and thiourea (0.5 g) and then the mixture was cooled to 5° C.

To the mixture was added zinc powder (1.3 g), and the mixture was stirred for an hour at 5° C. The resulting mixture was poured into a mixture of ethyl acetate (160 ml) and a saturated aqueous solution (100 ml) of sodium chloride, and insoluble materials were filtered off. The organic layer was separated therefrom, washed with a saturated aqueous solution of sodium chloride, dried over magnesium sulfate and then concentrated to 15 ml. To the residue was added a solution of p-toluenesulfonic acid (0.6 g) in ethyl acetate (10 ml). The resulting precipitates were collected by filtration and dried to give benzhydryl 7-amino-3-methylenecepham-4-calboxylate p-toluenesulfonate (1.0 g).

EXAMPLE 5

To N,N-dimethylformamide (20 ml) were added thiourea (0.76 g), zinc powder (0.5 g) and a solution of ammonium chloride (0.67 g) in water (3 ml). To the mixture was added benzhydryl 7-phenylacetamido-3-chloromethyl-3-cephem-4-carboxylate (2.67 g) under cooling to −15° C. with stirring, and the mixture was stirred for an hour at −15° to −10° C., and then filtered. To the filtrate were added ethyl acetate (100 ml) and water (100 ml), and the organic layer was separated therefrom. The organic layer was washed with water, dried over magnesium sulfate and then concentrated under reduced pressure. The residue was pulverized with diisopropyl ether to give benzhydryl 7-phenylacetamido-3-methylenecepham-4-carboxylate (2.2 g).

I.R. (Nujol): 3300, 1760, 1720, 1640, 1505 cm$^{-1}$

N.M.R. (DMSO-d$_6$, δ): 3.3–3.7 (4H, m), 5.18–5.7 (5H, m), 6.85 (1H, s), 9.07 (1H, d, J=8 Hz)

EXAMPLE 6

To a solution of benzhydryl 7-(5-benzamido-5-benzhydryloxycarbonylvaleramido)-3-hydroxymethyl-3-cephem-4-carboxylate (8.1 g) in methylene chloride (50 ml) was added phosphorus pentachloride under cooling to −20° C., and pyridine (0.95 g) was added dropwise thereto at the same temperature with stirring.

The mixture was stirred for 30 minutes at −20° to −10° C., and then water (50 ml) was added thereto. The organic layer was separated therefrom and adjusted to pH 6.0 with an aqueous solution of sodium bicarbonate. The organic layer was separated therefrom, washed with a saturated aqueous solution of sodium chloride and concentrated under reduced pressure to give benzhydryl 7-(5-benzamido-5-benzhydryloxycarbonylvaleramido)-3-chloromethyl-3-cephem-4-carboxylate.

Thus obtained compound was dissolved in N,N-dimethylformamide (30 ml) and cooled to −10° C. To the mixture were added a solution of ammonium chloride (1.4 g) in water (3 ml), thiourea (1.9 g) and zinc powder (1.6 g) and the mixture was stirred for an hour at −15° to −10° C. The reaction mixture was poured into a mixture of ethyl acetate (200 ml) and a saturated aqueous solution (200 ml) of sodium chloride, the resulting mixture was filtered. The organic layer was separated from the filtrate, washed with a saturated aqueous solution of sodium chloride, dried over magnesium sulfate and then concentrated under reduced pressure. The residue was dissolved in acetone (30 ml), and thus obtained solution was added to diisopropyl ether (250 ml). The resulting precipitates were collected by filtration and dried to give benzhydryl 7-(5-benzamido-5-benzhydryloxycarbonylvaleramido)-3-methylenecepham-4-carboxylate (6.7 g).

I.R. (Nujol): 3270, 1775, 1730, 1645 cm$^{-1}$

N.M.R. (DMSO-d$_6$, δ): 1.3–2.6 (6H, m), 3.38 (2H, m), 4.63 (1H, m), 4.9–5.7 (5H, m), 6.83 (1H, s), 6.88 (1H, s), 7.4 (23H, m), 7.93 (2H, m), 8.83 (2H, m)

EXAMPLE 7

To N,N-dimethylformamide (600 ml) were added thiourea (29.4 g) and a solution of ammonium chloride (25.8 g) in water (64 ml), and the mixture was cooled to 0° C. To the mixture was added zinc powder (18.3 g). The mixture was cooled to −15° C., and benzhydryl 7-amino-3-chloromethyl-3-cephem-4-carboxylate (80.0 g; purity 95.5%) was added thereto, and then the mixture was stirred for an hour at −15° to −10° C. and poured into a mixture of ethyl acetate (3.5 l) and an aqueous solution of sodium chloride (2 l). An insolble material was filtered off. The organic layer was separated out, washed with water, dried over magnesium sulfate and concentrated to about 700 ml. To the concentrate was added a solution of p-toluenesulfonic acid (40.4 g) in ethyl acetate (300 ml). The mixture was stood in a refrigerator to give benzhydryl 7-amino-3-methylenecepham 4-carboxylate p-toluenesulfonate (105.08 g) (Purity: 83.3%) in a yield of 86.0%).

REFERENCE 1

Phosphorus pentachloride (1 g) was suspended in methylene chloride (20 ml). The suspension was cooled to −5° C. To the suspension was added dropwise pyridine (0.31 ml) and the mixture was stirred for 20 minutes under ice-cooling. The reaction mixture was cooled to −30° C. and benzhydryl 7-phenylacetamido-3-methylenecepham-4-carboxylate (2 g) was added thereto. The mixture was stirred for an hour at −20° to −10° C. To the mixture was added methanol (5 ml) at −30° C. and the mixture was stirred for an hour at −10° C. To the reaction mixture was added cold water (30 ml). The organic layer was separated out, washed with an aqueous solution of sodium bicarbonate and an aqueous solution of sodium chloride, dried over magnesium sulfate and evaporated to dryness. The residue was dissolved in ethyl acetate (50 ml). To the solution was added a solution of p-toluenesulfonic acid (0.7 g) in ethyl acetate. The resulting precipitates were collected by filtration, washed with ethyl acetate and dried to give benzhydryl 7-amino-3-methylenecepham-4-carboxylate p-toluenesulfonate (1.3 g).

REFERENCE 2

Phosphorus pentachloride (3.0 g) was suspended in methylene chloride (50 ml). To the suspension was added dropwise pyridine (1.2 g) under ice-cooling and stirring, which was continued for 20 minutes at −5° C. The mixture was cooled to −30° C. and benzhydryl 7-(5-benzamido-5-benzhydryloxycarbonylvaleramido)-3-methylenecepham-4-carboxylate (5.0 g) was added thereto. The mixture was stirred for an hour at −20° to −10° C. and cooled to −30° C. To the above mixture was added methanol (10 ml) at a time and the mixture was stirred for an hour at −20° to −10° C. To the reaction mixture was added water (50 ml). The organic layer was separated out and an aqueous solution (50 ml) of sodium chloride was added thereto. The mixed solution was adjusted to pH 6.5 with an aqueous solution of sodium bicarbonate. The organic layer was separated out, dried over magnesium sulfate and concentrated under reduced pressure. The residue was dissolved in ethyl acetate (20 ml). To the solution was added a solution of p-toluenesulfonic acid (1.5 g) in ethyl acetate (20 ml). The resulting precipitates were collected by filtration, washed with ethyl acetate and dried to give benzhydryl 7-amino-3-methylenecepham-4-carboxylate p-toluenesulfonate (1.5 g).

What we claim is:

1. A new process for preparing 3-methylenecepham compounds of the formula:

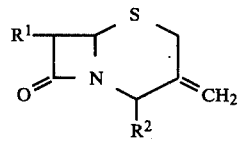

wherein
$R^1$ is amino or a protected amino group, and
$R^2$ is a carboxy or a protected carboxy group, or a salt thereof,
which comprises reducing a compound of the formula:

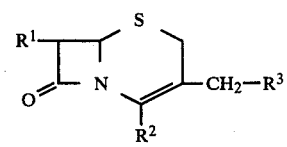

wherein
$R^1$ and $R^2$ are each as defined above, and
$R^3$ is halogen or heterocyclicthio which may have suitable substituent(s), or a salt thereof, with a combination of a metal selected from the group consisting of zinc, tin and iron, and an ammonium salt of an acid selected from the group consisting of ammonium halide, ammonium carbonate and ammonium acetate.

2. The process according to claim 1, in which the metal is zinc.

3. The process according to claim 2, in which the ammonium salt of an acid is ammonium halide.

4. The process according to claim 3, in which ammonium halide is ammonium chloride.

5. The process according to claim 4, in which the reaction is carried out in the presence of N,N-dimethylformamide.

6. The process according to claim 5, in which the reaction is carried out in the presence of thiourea.

7. The process according to claim 1, in which $R^3$ is halogen.

8. The process according to claim 1, in which $R^3$ is heterocyclicthio which may have suitable substituent(s).

* * * * *